(12) United States Patent
Norin

(10) Patent No.: US 8,771,971 B2
(45) Date of Patent: Jul. 8, 2014

(54) METHODS AND KITS FOR MEASUREMENT OF LYMPHOCYTE FUNCTION

(75) Inventor: Allen J. Norin, Pomona, NY (US)

(73) Assignee: The Research Foundation of State University of New York, Albany, NY (US)

( * ) Notice: Subject to any disclaimer, the term of this patent is extended or adjusted under 35 U.S.C. 154(b) by 1208 days.

(21) Appl. No.: 12/375,135

(22) PCT Filed: Jul. 30, 2007

(86) PCT No.: PCT/US2007/016971
§ 371 (c)(1),
(2), (4) Date: Apr. 12, 2010

(87) PCT Pub. No.: WO2008/013975
PCT Pub. Date: Jan. 31, 2008

(65) Prior Publication Data
US 2010/0190155 A1    Jul. 29, 2010

Related U.S. Application Data

(60) Provisional application No. 60/834,038, filed on Jul. 28, 2006.

(51) Int. Cl.
*G01N 33/53* (2006.01)
*G01N 33/553* (2006.01)

(52) U.S. Cl.
USPC ............ 435/7.24; 435/2; 435/7.1; 435/372.1; 435/372.2; 435/375; 436/522; 436/523; 436/526; 436/538; 436/63; 436/174; 422/430

(58) Field of Classification Search
USPC ............ 435/2, 7.1, 7.23, 7.24, 8, 375, 287.2, 435/372.1, 372.2; 436/522, 523, 524, 526, 436/528, 538, 10, 63, 64, 171, 172, 174; 422/430
See application file for complete search history.

(56) References Cited

U.S. PATENT DOCUMENTS

| | | | |
|---|---|---|---|
| 5,374,531 A * | 12/1994 | Jensen | 435/7.24 |
| 6,495,333 B1 | 12/2002 | Willmann et al. | |
| 6,630,316 B1 * | 10/2003 | Wier | 435/7.24 |
| 7,563,584 B2 * | 7/2009 | Perez et al. | 435/7.2 |
| 2002/0150952 A1 * | 10/2002 | Sottong et al. | 435/7.21 |
| 2005/0079555 A1 | 4/2005 | Willmann et al. | |

FOREIGN PATENT DOCUMENTS

WO     WO 97/36008     10/1997

OTHER PUBLICATIONS

Suni M.A. et al., "Detection of Antigen-Specific T Cell Cytokine Expression in Whole Blood by Flow Cytometry", *Journal of Immunological Methods* 212(I):89-98 (1998), XP-002545635.

* cited by examiner

*Primary Examiner* — Gail R Gabel
(74) *Attorney, Agent, or Firm* — Scully, Scott, Murphy & Presser, P.C.

(57) ABSTRACT

The present invention provides simple and rapid methods for measuring the function of a desired subset of lymphocytes, for example, T cells, B cells or NK cells. In addition, the present invention provides an all-in-one kit that contains reagents which permit a rapid and reliable analysis of the functions of T cells, B cells and NK cells obtained directly from whole blood or cord blood.

19 Claims, No Drawings

METHODS AND KITS FOR MEASUREMENT OF LYMPHOCYTE FUNCTION

CROSS-REFERENCE TO RELATED APPLICATIONS

This application claims the benefit of U.S. Provisional application No. 60/834,038 filed on Jul. 28, 2006.

FIELD OF THE INVENTION

The invention relates to methods for determining the functions of lymphocytes. The invention also relates to test kits used in performing such methods.

BACKGROUND OF THE INVENTION

The immune system is central to control of infectious diseases and cancer. Lymphocytes, a class of white blood cells, are critical cell types that are responsible for the activities of the immune system. Lymphocytes are divided into three major categories, T lymphocytes, NK cells and B lymphocytes. Overall assessment of the function of lymphocytes is important in determining the status of the immune system, in particular, immunodeficiency caused by genetic factors, infectious disease such as (HIV), drugs following transplantation, stress, aging, or nutritional deprivation.

Lymphocytes, which are usually in a metabolically inactive or resting state in the peripheral blood, express receptors on the cell surface that bind specific antigens. Exposure to an antigen results in metabolic activation and subsequent expansion of the population of the lymphocytes that are reactive to that antigen (clonal or oligoclonal response). Measurement of the response of the immune system to a specific antigen can be useful, for example, in diagnosis of infectious disease, hypersensitivity to certain agents, exposure to immunologically reactive drugs, assessing responses to vaccination or responses to an organ or tissue transplant. However, it is difficult to measure clonal responses since very few clones of cells (about 1 in $10^6$ may exist in a ml of blood) may respond to an antigen. This has led to assays where a polyclonal activator, such as Phytohemagglutinin (PHA), is used as a surrogate stimulant thus allowing the detection of increased function in a larger number of cells.

The function of B lymphocytes or their response to a specific antigen can be assessed by measuring the level of specific antibody in bodily fluids such as blood, saliva or urine. However methods of detecting antibody from a single clone of B lymphocytes in peripheral blood are difficult and time consuming. The function of T lymphocytes or their response to specific antigens is also difficult to measure. Measurement of the functions of T lymphocytes or T cells is complicated by a number of factors. First, there are several different subsets of T cells with different functions. These subsets have been classified in part by the expression of characteristic cell surface markers and in part by a variety of functional assays including measurement of cytokines. Second, T cells respond to antigens only when they are presented by other cells in the context of major histocompatibility antigens on the surface of the presenting cell. Third, many of the functions of T cells depend on cell-cell contact with effector cells or the functions are fairly localized. Current methods for measuring immune function are tedious, time consuming, and poorly adapted to the clinical laboratory setting.

Methods that are currently used for measurement of immune function include: methods based on measuring the increase in activation markers, methods based on measuring the proliferation of lymphocytes, methods based on measuring DNA synthesis, methods based on measurement of cytotoxic activity or secretion of cytokines or other soluble factors, and methods used in vivo, such as skin tests.

Direct measurement of responses of lymphocytes has included proliferation assays, cytotoxicity assays, and measurement of cytokines. In general, these methods require separation of white cells from the original sample followed by incubation with antigen or mitogen. Measurement of the function of specific subsets of lymphocytes requires extensive and expensive manipulations prior to the assay. The requirement for antigen presenting cells then means that additional cells have to be added back to the culture. Lymphoproliferation assays are based on division of responding cells and are typically performed by incorporation of radioactive or nonradioactive labeled precursors of DNA synthesis. DNA synthesis or other proliferation assays take 2-10 days and are subject to significant variability based on the specific technique and the reagents used in the assay. Cytotoxic tests also require significant cell manipulation and time, and require appropriate target cells.

SUMMARY OF THE INVENTION

The invention provides a convenient, less expensive and reliable method and an all-in-one kit for analyzing the function of various lymphocytes.

The method provided by the invention involves contacting a sample containing lymphocytes with a stimulating agent for a time sufficient to activate the lymphocytes including a desired subset of lymphocytes. The lymphocytes of interest are then separated from the remainder of the sample by employing an isolation agent specific for the subset of lymphocytes, wherein the isolation agent typically contains a specific binding agent immobilized on a solid support material. Alternatively, the lymphocytes of interest are separated from the remainder of the sample first, before incubating with a stimulating agent. In either approach, the stimulated and separated lymphocytes are then analyzed using a variety of approaches to determine their function, for example, by measuring the ATP content of the cells of interest following cell lysis. This result is compared to the ATP content of unstimulated lymphocytes, which establishes baseline function.

In certain preferred embodiments, the present method employs a single agent that serves both as a stimulating agent to activate a subset of lymphocytes of interest and as an isolation agent to permit isolation of the subset of lymphocytes of interest.

In a preferred embodiment, the present invention provides a method for determining the function of T cells by employing magnetic beads coated with anti-CD3. Such coated beads serve the dual function of stimulant and isolation agent. Furthermore, anti-CD28 antibody coated beads may also be added to provide costimulation.

In another embodiment, the present invention provides a method for determining the function of B cells by employing Pansorbin$^R$ or magnetic beads coated with Protein A, which activates B cells by cross-linking immunoglobulin (Ig) molecules on the B cell surface and permits subsequent isolation of B cells by using a magnet.

In still another embodiment, the present invention provides a method for determining the function of NK cells by employing magnetic beads coated with an anti-CD16 antibody. The anti-CD16 antibody activates NK cells by cross-linking CD16 molecules on the surface of NK cells, and permits the subsequent isolation of NK cells by a magnet. NK cells may also be activated by lymphokines such as IL15 or IL2.

In a further aspect, the present invention provides a kit for performing the methods of the invention. The kit contains reagents for analyzing the function of one or more subsets of lymphocytes of interest.

In addition to methods and compositions described above for determining the function of lymphocytes in short term culture assays, lymphocytes can be propagated using a stimulating agent described herein, and the expanded population of lymphocytes can be used for analysis of functions that are expedited by such expansion. For example, the detection and quantitation of antibody produced by only one or several clones of B cells would be greatly facilitated by expansion of said clone(s). Additionally, lymphocytes can be propagated using a stimulating agent described herein, and the expanded population of lymphocytes can be used for therapeutic purposes.

DETAILED DESCRIPTION OF THE INVENTION

The present invention provides simple and rapid methods for measuring the function of a desired subset of lymphocytes, for example, T cells, B cells or NK cells. In addition, the present invention provides an all-in-one kit containing reagents that permit a rapid and reliable analysis of the functions of T cells, B cells and/or NK cells obtained directly from whole blood or cord blood.

In a first aspect of the present invention, a method is provided for measuring the function of a desired subset of lymphocytes.

According to the method of the present invention, a sample containing lymphocytes, for example, a sample of whole blood or cord blood, can be obtained from a subject. The sample is incubated with a stimulating agent for a time sufficient for the stimulating agent to activate the lymphocytes or at least the desired subset of lymphocytes. Afterwards, the subset of lymphocytes of interest are separated from the remainder of the sample, preferably by employing a binding agent specific for the subset of lymphocytes of interest, wherein the binding agent is immobilized on a solid support to facilitate the separation. Alternatively, a desired subset of lymphocytes are first isolated from other cells in the sample by employing a binding agent specific for this subset of lymphocytes, and then the isolated lymphocytes are incubated with a stimulating agent for a time sufficient to activate the lymphocytes.

In certain preferred embodiments, the present method employs a single agent that serves both as a stimulating agent to activate a subset of lymphocytes of interest and as a binding or separation agent to permit isolation of the subset of lymphocytes. The separated and stimulated lymphocytes can then be analyzed using a variety of approaches to determine their function.

In a preferred embodiment, the function of stimulated lymphocytes is compared to the function of unstimulated lymphocytes from the same sample of blood. The activation of lymphocytes by a polyclonal activator is thought to be additive to the quantity of cells that are spontaneously active in a blood sample, since polyclonal activators neither inhibit nor stimulate cells that are already functionally active. For example, if it was determined that 1% of the lymphocytes were undergoing DNA synthesis in an unstimulated sample and a polyclonal activator caused 20% of the (inactive) cells to undergo DNA synthesis, then 21% of the cells would be undergoing DNA synthesis in the stimulated culture. Accordingly, it is believed that the activities and responsiveness of the immune system of a subject are more accurately reflected by the difference between the function of stimulated lymphocytes and the function of unstimulated lymphocytes, rather than the function of stimulated lymphocytes itself. If baseline values are not used, in some cases, the degree of stimulation can over- or under-estimated.

Lymphocytes

Lymphocytes of interest in the context of the present invention include T lymphocytes, B lymphocytes, and NK cells, as well as subsets of T cells, such as T helper cells and cytotoxic T cells.

Stimulating Agents

As used herein, "stimulating agents" or "stimulants" refer to substances that interact with one or more subsets of lymphocytes of interests whereby the interaction results in a change in the physiologic state of the cells and induces a functional activity or a different gene expression pattern in the stimulated cells, as compared to the unstimulated lymphocytes. For example, a stimulant can cause resting lymphocytes to become activated, manifesting certain activities that can be measured as reflecting an increase in the function of the lymphocytes of interest.

Stimulating agents include mitogens that interact with all the lymphocytes of a particular subset (e.g., all T cells, or all B cells) and induce activation and proliferation of these lymphocytes. Mitogens for different populations of lymphocytes are known and include lectins, antibodies or other substances that bind to lymphocyte cell surface receptors involved in signal transduction such as CD3 on T lymphocytes or IgM on B lymphocytes, growth factors and lymphokines, phorbol esters, phytohemagluttinin (PHA), Concanavalin A (Con A), and other biochemical substances that are known to those skilled in the art.

Stimulating agents also include antigens that interact through specific receptors on limited subpopulations of cells within a subset of lymphocytes. Each lymphocyte has on its cell surface a receptor for a specific antigen or molecule. For B lymphocytes, the cell surface receptor is antibody that is membrane bound. For T lymphocytes, the cell surface receptor is the T cell receptor that complexes with the CD3 proteins on binding of antigen that is presented in the context of major histocompatibility molecules on the surface of another cell.

In the context of the present invention, a stimulating agent can be a polyclonal activator.

According to the present invention, stimulating agents suitable for use in assaying the function of T cells include agents that bind and crosslink receptors involved in signal transduction and are specifically expressed on T cells. In a preferred embodiment, the stimulating agent includes an anti-CD3 antibody, or an anti-CD3 antibody in combination with an anti-CD28 antibody, or an antigen-binding fragment of any of the above antibodies, or a combination thereof. The antibody or a fragment thereof can be attached to a solid support. For example, a stimulating agent can be an anti-CD3 antibody bound to beads. Another example of a stimulating agent is an anti-CD3 antibody bound to beads, in combination with a cytokine such as IL-2.

Stimulating agents suitable for use in assaying the function of B cells include antibodies and agents that bind and crosslink receptors involved in signal transduction that are expressed on B cells. In a specific embodiment, the stimulating agent is the polyclonal activator, Pansorbin$^R$. Pansorbin$^R$ is a source of immobilized Protein A, which crosslinks Ig molecules on the surface of B cells and leads to the activation of the B cells. In another embodiment, the stimulating agent is Protein A bound to beads. In still another specific embodiment, the stimulating agent is an anti-IgM antibody bound to beads.

For NK cells, suitable stimulating agents include an anti-CD16 antibody or an antigen-binding fragment thereof, which is bound to beads, the Haymaker protein bound to beads, IL-2, and IL-15, among others. The Haymaker protein has been identified as a ligand for receptors on NK cells. See, e.g., Das et al., "*Preferential interaction of a novel tumor surface protein (p38.5) with a receptor on naive NK cells*", J. Exp. Med. 185: 1735-1742 (1997); Das et al., "*Genetic identity and expression of p38.5 (Haymaker) in human malignant and non-malignant cells*", Int J Cancer 94:800-06 (2001); and Das et al., "*Difference in Target Cell Recognition of Naive and Activated Human NK Cells: Role of Haymaker (p38.5) in Tumoricidal Activity*", Human Immunol. 66: 241-51 (2005).

The time period for which the sample is incubated with the stimulant should be sufficient to activate the desired subset or subsets of lymphocytes. Generally speaking, the sample can be incubated with a stimulant for a period of about 4 to 48 hours, or preferably 4 to 20 hours, or more preferably, about 5 to 18 hours, or even more preferably, about 17 to 18 hours. The precise time period of incubation may vary depending on the stimulant and the subset of lymphocytes.

Separation of Lymphocytes

Either before or after incubation with a stimulating agent, a desired subset of lymphocytes is separated from the remainder of the sample by employing a binding agent that specifically binds this subset of lymphocytes. Specific binding agents include antibodies capable of recognizing determinants or receptors specifically expressed on the subset of lymphocytes of interest, or antigen-binding fragments of such antibodies.

The binding agent is typically immobilized on a solid material to facilitate the separation. A binding agent immobilized on a solid support is also referred to herein as an "isolation agent". A variety of solid support materials can be used e.g., polystyrene, nylon or agarose beads, and are well known to those skilled in the art. In a preferred embodiment, the solid support material is a magnetic bead. Techniques for attaching a binding agent such as an antibody to the beads are known to those skilled in the art. Suitable techniques include cross-linking, covalent binding, or physical adsorption.

In accordance with the present invention, the stimulating agent can be the same material as the isolation agent for the purpose of analyzing a particular subset of lymphocytes. That is, the same material can serve both as the stimulating agent and the isolation agent in the present method.

For example, magnetic beads coated with anti-CD3 can be used as a dual agent for both stimulating and isolating T cells. In another example, magnetic beads coated with anti-CD3 and beads coated with, for example, anti-CD28 antibody, can be used to both stimulate and isolate T cells. Such a mixture of beads can directly stimulate T cells through the CD3 complex and provide co-stimulation via CD28 cross-linking, and allow for isolation of CD3$^+$ T cells using a magnet. According to the present invention, the stimulation achieved by the combination of anti-CD3 and anti-CD28 antibodies is thought to reflect T cell activation in a physiologically relevant setting. In addition, the dual function of the magnetic beads coated with anti-CD3 antibodies as both the stimulant and the isolation agent provides a more rapid and convenient analysis of lymphocyte function.

Similarly, magnetic beads coated with Protein A, as well as beads coated with an anti-IgM antibody, can be used both as a polyclonal B cell activator and as an isolation agent for separating these cells from the remainder of the sample by magnet. Magnetic beads coated with anti-CD16 can serve both to activate NK cells through crosslinking CD16 molecules on the surface of NK cells and to separate the NK cells from other cells in blood by use of a magnet.

In other embodiments of the present invention, the isolation agent is different from the stimulating agent employed. For example, T cells can be stimulated with anti-CD3 and anti-CD28 antibodies bound to a solid support, and are subsequently isolated with anti-CD3, anti-CD4 and/or anti-CD8 antibody coated magnetic beads. B cells can be activated with Pansorbin$^R$, and are subsequently isolated using magnetic beads coated with anti-CD19 or anti-CD20 and a magnet. NK cells can be activated with IL-2 or IL-15, and are subsequently isolated using magnetic beads coated with anti-CD16.

In a preferred embodiment, antibody coated magnetic beads used for stimulation and/or isolation are smaller than lymphocytes. For example, lymphocytes are typically 7 to 10 microns in size, and suitable beads for use in stimulation and/or isolation may be of a size in the range of one to five microns, preferably one to three microns, and more preferably one to two microns. Small beads, especially one to two micron magnetic beads, have a significant advantage over magnetic beads that are larger than cells in that the small beads are able to more effectively stimulate and isolate lymphocytes.

Either prior to or after stimulation, a lymphocyte-containing sample is contacted with an isolation agent, e.g., magnetic beads coated with a binding agent specific for a desired subset of lymphocytes. A complex is formed between the desired lymphocytes and the binding agent/magnetic beads. The unbound cells and sera can be removed from the specifically bound cells by typically employing a magnet.

In the case of whole blood or cord blood, one can wash the complex to remove cells that are trapped or bound nonspecifically. A variety of solutions (e.g., 0.15M ammonium chloride, 1.0M potassium carbonate, 0.1M EDTA, pH 7.2) that specifically lyse red blood cells, platelets, or other potential contaminants, are known to those skilled in the art. In addition, solutions that contain other substances, such as proteins, sugars, or salts or that are of specific pH values, can be useful in reducing the nonspecific binding of other cell types and in eliminating or lysing cell types that are not of interest.

Determination of the Function of Separated Lymphocytes

In one embodiment, the separated and stimulated cells are lysed and the level of ATP is measured as indicative of the function of the lymphocytes. It is well known that ATP levels are indicative of metabolic activity. The metabolic activity of cells that respond to a stimulant increases significantly and that this increase is reflected in significant increases in the level of ATP.

A variety of lysis solutions exist and are well known to those in the art, including distilled water, solutions containing detergents such as Triton-X100, NP-40, DTAB, THESIT, and buffered solutions such as HEPES containing 0.1M benzalkonium chloride or preferably a buffer containing 10 mM Trizma base. The material and the solution chosen for lysis should not interfere with the system for measuring ATP, do not contain ATP, and do not degrade ATP. For example, to prevent the degradation of ATP, the pH of the lysis buffer is adjusted so as to inhibit endogenous ATPase activity, preferably adjusted to a value in the range of pH 9 to 12, preferably about pH 10 to about pH 11.

Following lysis of the cells, the level of ATP in the solution is measured by using a variety of approaches. In one embodiment, the ATP in the lysate is measured by the addition of a small quantity of said lysate to a solution containing firefly luciferase and luciferin in the presence of magnesium ions. Particularly, ATP levels can be measured very sensitively using the bioluminescent reaction of firefly luciferase with luciferin, as described by, for example, Leach and Webster, *Meth. Enzymol.* 133: 51-70, (1986), which is incorporated herein by reference. See, also, U.S. Pat. No. 6,630,316, incorporated herein by reference. ATP can also be measured by other means including immunochemical or biochemical reaction systems.

In another embodiment, the separated and stimulated lymphocytes of interest are lysed and RNA is isolated from the lysed cells for use in quantitative RT-PCR to detect changes in the expression of genes of interest, for example, genes encoding cytokine such as IL-2 and IL-4, genes encoding cytokine receptors, genes encoding effector molecules such as perforin, Granzyme B, gamma interferon, and signal transduction molecules such as NF kappa B and NFAT.

In still another embodiment, the stimulated and separated lymphocytes of interest are analyzed, without cell lysis, for cell surface activation markers by fluorescent activated flow cytometry, including but not limited to CD25 or CD69, and intracellular markers such as IL-2 or perforin.

Kits

In a further aspect of the present invention, a kit is provided for performing the methods of the invention.

The kit provided by the present invention contains reagents for determining the function of one or more subsets of lymphocytes of interest. More specifically, the kit contains one or more stimulants that activate one or more subsets of lymphocytes of interest; one or more binding agents or isolating agents for isolating a subset or subsets of lymphocytes of interest; a lysis solution; and reagents for assaying the functional activity of the lymphocytes of interest, such as luciferin, a luciferase; at least one ATP calibration reagent. The kit may contain additional materials suitable for performing the methods of the invention, including multiwell stripes, tissue culture medium, and the like.

Propagation of Lymphocytes

In addition to methods and compositions described above for determining the function of lymphocytes in short term culture assays, lymphocytes can be propagated using a stimulating agent described herein, and the expanded population of lymphocytes can be used for analysis of functions that are expedited by such expansion. Additionally, lymphocytes can be propagated using a stimulating agent described above, and the expanded population of lymphocytes can be used for therapeutic purposes. For example, a sample containing lymphocytes is incubated with a stimulating agent for a time sufficient for the stimulating agent to activate the lymphocytes or at least the desired subset of lymphocytes, which results in a proliferation of the lymphocytes or a desired subset of lymphocytes. The activated and proliferated cells can be isolated as described above, and used for therapeutic purposes.

The following examples are provided to describe the invention in further detail. These examples are intended to illustrate specific applications of the methods of the invention and should in no way be construed as limiting the invention.

EXAMPLES

Example 1

Determination of T Cell Function

A whole blood sample is incubated with anti-CD3 and anti-CD28 antibody coated one micron magnetic beads for 18 hours. These beads directly stimulate CD3+ cells and provided co-stimulation via CD28 cross-linking, as well as subsequently allowing for magnetic bead isolation of CD3+ and CD28+ T cells. The T cells are separated from the sample by a magnet, lysed and assayed for ATP content using standard reagents. An unstimulated whole blood sample is cultured for 18 hours without the above beads and the lymphocytes are isolated with one micron anti-CD3 coated magnetic beads and assayed for ATP. Stimulation is calculated by the following formula: Stimulation, ng/ml ATP=Cells cultured with beads for 18 hours, ng/ml ATP−Cells not cultured with beads (unstimulated cells), ng/ml ATP.

In a separate experiment, a whole blood sample was incubated with PHA (3 µg/ml) for 18 hours. An unstimulated whole blood sample was cultured without PHA for 18 hours as controls. The cells are then mixed with Dynal$^R$ magnetic beads coated with an anti-CD4 antibody. The T cells were separated from the sample by a magnet, lysed and assayed for ATP content using standard reagents. Stimulation was calculated by the following formula: Stimulation, ng/ml ATP=Cells cultured with PHA, ng/ml ATP−Cells cultured without PHA (unstimulated cells), ng/ml ATP. The results are shown in Table 1.

Example 2

Determination of B Cell Function

The washed buffy coat obtained from a whole blood sample was incubated with a polyclonal activator for B cells, Pansorbin$^R$. Buffy coat rather than whole blood must be used to assay B lymphocyte function with stimulants such as Protein A and anti-IgM since the Igs in the plasma would bind to these agents thereby preventing the stimulant from binding to and activating the B cells. After 18 hours of incubation, the B cells were isolated by one micron magnetic beads coated with anti-CD19 or anti-CD20 antibody and a magnet. The isolated B cells were lysed and assayed for ATP content. The results are shown in Table 1 and Table 2.

In a separate experiment, washed buffy coat obtained from a whole blood sample was incubated with Protein A coated one micron magnetic beads. After 18 hours of incubation, the B cells were isolated using a magnet and were lysed to analyze the ATP content. An unstimulated buffy coat sample was cultured for 18 hours without the Protein A beads, and the lymphocytes were isolated with one micron Protein A coated magnetic beads and assayed for ATP. Stimulation was calculated by the following formula: Stimulation, ng/ml ATP=Cells cultured with beads for 18 hours, ng/ml ATP−Cells not cultured with beads (unstimulated cells), ng/ml ATP. The results are shown in Table 1 and 2.

Example 3

Determination of NK Cell Function

A whole blood sample is incubated with a polyclonal activator for NK cells, either IL-2 or IL-15. After 18 hours incubation, the NK cells are separated from the sample with one micron magnetic beads coated with an anti-CD16 antibody prior to lysis and analysis for ATP content. An unstimulated whole blood sample is cultured for 18 hours without the cytokines and the lymphocytes isolated with one micron anti-CD16 coated magnetic beads and assayed for ATP. Stimulation is calculated by the following formula: Stimulation, ng/ml ATP=Cells cultured with beads for 18 hours, ng/ml ATP−Cells not cultured with cytokines (unstimulated cells) ng/ml ATP.

Alternatively, a whole blood sample is incubated with anti-CD16 antibody coated one micron magnetic beads for 18 hours. At the end of an 18-hour culture period, NK cells are isolated from the sample by using a magnet. The cells are then lysed and the ATP content is determined. An unstimulated whole blood sample is cultured for 18 hours without the anti-CD16 coated beads and the lymphocytes isolated with one micron anti-CD16 coated magnetic beads and assayed for ATP. Stimulation is calculated by the following formula: Stimulation, ng/ml ATP=Cells cultured with beads for 18 hours, ng/ml ATP–Cells not cultured with beads (unstimulated cells) ng/ml ATP.

It is understood that the examples and embodiments described herein are for illustrative purposes only and that various modifications and changes in light thereof will be suggested to persons skilled in the art and are to be included within the purview of this application and the scope of the appended claims.

TABLE 1

Comparison of B Cell Stimulation with Pansorbin ® and T cell Stimulation with PHA*

| Subject | B cell Function Assay | | | T cell Function Assay | | |
|---|---|---|---|---|---|---|
| | Unstim | Pansorbin ® | Difference | Unstim | PHA | Difference |
| A. | 127 | 429 | 302 | 36 | 362 | 326 |
| B. | 152 | 205 | 53 | 5 | 134 | 129 |
| C. | 608 | >1000 | >392 | 79 | 364 | 285 |
| D. | 117 | 473 | 356 | 3 | 473 | 470 |

*Results are reported in ng/ml ATP. Subject "A" is a normal adult subjects "B-D" are children <12.

TABLE 2

Comparison of B Cell Stimulation with Pansorbin ® and Protein A Magnetic Beads from the Same Adult Subject*

| Stimulant | Unstimulated | Stimulated | Difference |
|---|---|---|---|
| Pansorbin ® | 117 | 367 | 250 |
| Protein A beads | 108 | 503 | 395 |

*Results are reported in ng/ml ATP

What is claimed is:

1. A method for determining the function of a selected subset of lymphocytes, comprising:
   contacting a sample containing subsets of lymphocytes with a stimulating agent configured to activate at least one selected subset of lymphocytes;
   contacting the sample with an isolation agent that specifically binds said stimulated selected subset of lymphocytes, wherein the isolation agent is coated onto magnetic beads of one to five microns and wherein the stimulating agent used to activate at least one selected subset of lymphocytes is the same agent as the isolation agent used to specifically bind the selected subset of lymphocytes;
   separating from the remainder of the sample, said selected subset of activated lymphocytes, which are bound to said isolation agent; and
   measuring cells from the separated subset of activated lymphocytes for functional activity, gene expression, or lymphocyte subset-specific activation marker, wherein the measurement is compared with that from unstimulated lymphocytes.

2. A method for determining the function of a selected subset of lymphocytes, comprising:
   contacting a sample containing subsets of lymphocytes with an isolation agent that specifically binds said selected subset of lymphocytes to separate said selected subset of lymphocytes from the remainder of the sample, wherein the isolation agent is coated onto magnetic beads of one to five microns;
   contacting the separated, selected subset of lymphocytes with a stimulating agent for a time sufficient to activate said lymphocytes, wherein the stimulating agent is configured to activate the at least one selected subset of lymphocytes and is the same agent as the isolation agent used to specifically bind the selected subset of lymphocytes; and
   measuring the activated and isolated subset of lymphocytes for a functional activity, gene expression, or lymphocyte subset-specific activation marker to determine the function of said selected subset of activated lymphocytes, wherein the measurement is compared with that from unstimulated lymphocytes.

3. The method of claim 1 or 2, wherein said selected subset of lymphocytes is composed of T lymphocytes.

4. The method of claim 3, wherein said isolation agent comprises the magnetic beads immobilized with an anti-CD3 antibody, an anti-CD28 antibody, an anti-CD4 antibody, an anti-CD8 antibody, an anti-T cell receptor antibody, an antigen-binding fragment of any of the foregoing antibodies, or a combination of any of the foregoing antibodies or fragments.

5. The method of claim 1 or 2, wherein the stimulating agent is coated onto magnetic beads.

6. The method of claim 5, wherein said stimulating agent is selected from the group consisting of phorbol esters, phytohemagluttinin (PHA), Concanavalin A (ConA), an anti-T cell receptor antibody bound to magnetic beads, an anti-CD3 antibody bound to magnetic beads, an antigen-binding fragment of an anti-CD3 antibody bound to magnetic beads, anti-CD28 antibody bound to magnetic beads, an antigen-binding fragment of anti-CD28 antibody bound to magnetic beads, an anti-CD3 antibody or antigen-binding fragment thereof bound to magnetic beads in combination with interleukin 2 (IL-2), and a combination thereof.

7. The method of claim 5, wherein said stimulating agent is selected from the group consisting of Pansorbin$^R$, Protein A, an anti-IgM antibody or an antigen-binding fragment thereof bound to beads, and a combination thereof.

8. The method of claim 5, wherein said stimulating agent is selected from the group consisting of interleukin 2 (IL-2), interleukin 15 (IL-15), Haymaker, an anti-CD16 antibody or an antigen-binding fragment thereof, and a combination thereof.

9. The method of claim 1 or 2, wherein said selected subset of lymphocytes is composed of B lymphocytes.

10. The method of claim 9, wherein said isolation agent is Protein A bound to magnetic beads, an anti-CD19 antibody or an antigen-binding fragment thereof bound to magnetic beads, an anti-CD20 antibody or an antigen-binding fragment thereof bound to magnetic beads, an anti-IgM antibody or an antigen-binding fragment thereof bound to magnetic beads.

11. The method of claim 1 wherein the magnetic beads are one to two micron.

12. The method of claim 2 wherein the magnetic beads are magnetic beads of one to two microns.

13. The method of claim 1 or 2, wherein said selected subset of lymphocytes is composed of natural killer (NK) cells.

14. The method of claim 13, wherein said isolation agent is an anti-CD16 antibody or an antigen-binding fragment thereof, bound to magnetic beads.

15. The method of claim 1 or 2, wherein said sample is a whole blood sample obtained from a human subject.

16. The method of claim 1 or 2, wherein the selected subset of cells are lysed after stimulation and separation, and at least one of the following is measured: the level of adenosine triphosphate (ATP) from cell lysate, or the expression of a gene encoding interleukin 2 (IL-2), a cytokine receptor, perforin, Granzyme B, gamma interferon, nuclear factor (NF) kappa B, or nuclear factor of activated T cells (NFAT).

17. The method of claim 1 or 2, wherein the selected subset of cells is analyzed by fluorescent activated flow cytometry for an activation marker selected from the group consisting of CD25, CD69, IL-2, perforin and Gramzyme B.

18. A kit for determining the function of a selected subset of lymphocytes, comprising a stimulating agent configured to activate a selected subset of lymphocytes, an isolation agent that specifically binds and isolates said selected subset of lymphocytes, wherein the isolation agent is coated onto magnetic beads of one to five microns, wherein the stimulating agent used to activate the at least one selected subset of lymphocytes is the same agent as the coated isolation agent used to specifically bind the selected subset of lymphocytes, a lysis solution, and reagents for measuring the adenosine triphosphate (ATP) level from lysed lymphocytes, reagents for detecting changes in gene expression, or reagents for detecting activation markers based on flow cytometry.

19. A kit for propagating T cells, B cells or natural killer (NK) cells comprising a stimulating agent configured to activate a selected subset of lymphocytes, an isolation agent that specifically binds and isolates said selected subset of lymphocytes, wherein the isolation agent is coated onto magnetic beads of one to five microns, at least one of one micron anti-CD3/CD28 coated magnetic beads, one micron Protein A coated magnetic beads, and one micron anti-CD16 coated magnetic beads, respectively, wherein the stimulating agent used to activate the at least one selected subset of lymphocytes is the same agent as the coated isolation agent used to specifically bind the selected subset of lymphocytes.

* * * * *